(12) United States Patent
Laplaza et al.

(10) Patent No.: US 7,501,275 B2
(45) Date of Patent: Mar. 10, 2009

(54) YEAST TRANSFORMATION SYSTEM

(75) Inventors: Jose M. Laplaza, Sun Prairie, WI (US); Thomas W. Jeffries, Madison, WI (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 451 days.

(21) Appl. No.: 10/973,274

(22) Filed: Oct. 27, 2004

(65) Prior Publication Data

US 2006/0088911 A1  Apr. 27, 2006

(51) Int. Cl.
*C12N 1/15* (2006.01)
*C12N 15/00* (2006.01)
*C12N 15/11* (2006.01)

(52) U.S. Cl. ................. 435/254.23; 435/69.1; 536/23.1

(58) Field of Classification Search ........................ None
See application file for complete search history.

(56) References Cited

U.S. PATENT DOCUMENTS

| | | | |
|---|---|---|---|
| 4,959,317 A | 9/1990 | Sauer | |
| 6,379,943 B1* | 4/2002 | Graham et al. | 435/235.1 |
| 6,534,314 B1 | 3/2003 | Bouhassira et al. | |
| 6,534,315 B1 | 3/2003 | Bauer et al. | |
| 6,562,595 B2 | 5/2003 | Roemer et al. | |
| 6,723,562 B1 | 4/2004 | Ashikari et al. | |
| 2006/0148049 A1* | 7/2006 | Fukuchi et al. | 435/135 |

OTHER PUBLICATIONS

Yang, V.W. et al., "High-efficiency transformation of *Pichia stipitis* . . . replication sequence, ARS2," 1994, 4245-4254, vol. 60, No. 12, Applied and Environ. Microbiol.

Lu, P. et al., "Cloning and disruption of the beta-isopropylmalate dehydrogenase . . . recovery of the double auxotroph," 1998, 141-146, vol. 49, Appl. Microbiol. Biotechnol.

Agatep, R. et al., "Transformation of *Saccharomyces cerevisiae* by . . . (LiAc/ss-DNA/PEG) protocol," 1998, http://www.ciwemb.edu/labs/koshland/protocols/yeast/liac.html.

Tang, S., et al., "A transformation system for the nonuniversal CUG-ser codon usage species *Candida rugosa*," 2003, 231-238, vol. 52, J. of Microbiol. Methods.

Piontek, M., et al., "Two novel gene expression systems based on the yeasts *Schwanniomyces ocidentalis* and *Pichia stiptis*," 1998, 331-338, vol. 50, Appl. Mirobiol. Biotechnol.

Johansson & Hahn-Hagerdal, "Overproduction of pentose phosphate . . . using a CRE-loxP expression vector . . . in *Saccharomyces cerevesiae*," 2002, 225-231, vol. 19, Yeast.

Sugita & Nakase, "Non-universal usage of the leucine CUG codon and the molecular phylogeny of the genus *Candida*," 1999, 78-86, vol. 22, System. Appl. Microbiol.

Methods in Yeast Genetics (Kaiser et al., eds.), "Modified Lithium Acetate Yeast Transformation," 1994, 201-202, Cold Spring Harbor Laboratory Press.

Non-Conventional Yeasts in Genetics . . . (Wolf et al., eds.), "ADH1 disruption in *Pichia stipitis* by targeted restriction enzyme mediated integration," 2003, 221-228, Springer.

Vallejo et al., in PCR Primer (Dieffenbach & Dveksler eds.), "Mutagenesis and Synthesis of . . . Recombinant Genes using PCR," 1995, 603-612, Cold Spring Harbor Laboratory Press.

Tekaia, F., et al., "Genomic Exploration of the Hemiascomycetous Yeasts: 3. Methods and strategies used for sequence analysis and annotation," FEBS Letters (2000) 487:17-30.

* cited by examiner

*Primary Examiner*—Nancy Vogel
(74) *Attorney, Agent, or Firm*—John D. Fado; Lesley D. Shaw; Janet I. Stockhausen

(57) ABSTRACT

Disclosed are methods for obtaining expression of polypeptides in organisms employing alternative codon systems, and polynucleotides for use therein.

5 Claims, No Drawings

YEAST TRANSFORMATION SYSTEM

STATEMENT REGARDING FEDERALLY SPONSORED RESEARCH OR DEVELOPMENT

This invention was made with United States Government support from the United States Department of Agriculture, Forest Service, Forest Products Laboratory with programmatic funding to Research Work Unit 4712.

CROSS-REFERENCE TO RELATED APPLICATIONS

Not applicable.

INTRODUCTION TO THE INVENTION

*Pichia stipitis* is a yeast capable of fermenting xylose to produce ethanol. Because xylose is found abundantly in agricultural and wood residues, the ability of *P. stipitis* to convert xylose to ethanol may be exploited to expand ethanol production from residual biomass. However, progress in the development of genetically enhanced stains of *P. stipitis* that are suitable for use on a commercial scale has been hampered by the lack of a versatile transformation system for this species.

Transformation systems for yeast and fungi often employ auxotrophic hosts to select for transformants. This limits the number of available host strains. Auxotrophs are commonly generated by random or site-specific mutagenesis. Random mutagenesis creates mutational events in many genes other than the target. Random spontaneous or chemically generated ura3 mutants have been obtained with *P. stipitis*. Site-specific mutagenesis or targeted deletion has been successful with *P. stipitis* LEU2 using PsURA3 as the selectable marker in a ura3 background. The *P. stipitis* leu2, ura3 double auxotroph has been recovered. However, the resulting strain grows poorly and does not ferment xylose at a rate that is sufficient for commercial development (Lu, et al.; 1998; Yang et al., 1994). Targeted deletion or disruption of *P. stipitis* URA3 has not yet been demonstrated in the published literature. Also, the DNA sequence of some very useful auxotrophic selectable markers such as the native gene for *P. stipitis* URA3 include a number of restriction sites that make it difficult to manipulate vectors that contain this gene. Thus, previously demonstrated transformation systems, while very useful for research purposes, are not suitable for generating *P. stipitis* strains for industrial fermentations.

In an alternative to using auxotrophs as the basis for selecting recombinant yeasts, strains can be transformed with sequences encoding a protein that permits selection based on antibiotic resistance. This approach expands the range of suitable host strains available for use in developing genetically engineered yeasts. However, attempts to develop transformation systems based on antibiotic resistance have been largely unsuccessful in *P. stipitis*. Genes for antibiotic resistance (markers) must be translated faithfully from the DNA sequence carried on the vector into an active protein that will help the recipient host defend against the antibiotic. Characteristics of the *P. stipitis* translational machinery make heterologous expression of many drug resistance markers problematic. Development of a transformation system based on antibiotic resistance for yeast like *P. stipitis* would facilitate development of genetically enhanced *P. stipitis* strains.

SUMMARY OF THE INVENTION

The present invention provides a method of expressing in a *P. stipitis* cell a polypeptide containing leucine by introducing a polynucleotide encoding the polypeptide into the cell under conditions that allow polypeptide expression. The polynucleotide is one not natively associated with *P. stipitis* and may be a selected polynucleotide that does not natively contain a trinucleotide sequence encoding a CUG codon, a selected polynucleotide in which in-frame trinucleotide sequences encoding CUG codons are meant to encode serine, or a modified polynucleotide in which at least one trinucleotide sequence encoding a CUG codon is replaced with a sequence encoding a codon selected from the leucine encoding codons UUA, UUG, CUU, CUC and CUA. The polynucleotide is operably connected to a promoter functional in *P. stipitis* such that the polypeptide may be expressed in *P. stipitis* cells.

In another aspect, the present invention provides a method of expressing a polypeptide natively associated with *P. stipitis* in a cell having a leucine tRNA that recognizes the CUG codon by introducing a polynucleotide encoding the polypeptide into the cell under conditions that allow expression of the polypeptide. The polynucleotide is either a *P. stipitis* coding sequence that is selected because it lacks a trinucleotide sequence encoding a CUG codon or a polynucleotide that has been modified to replace at least one CUG codon with a sequence encoding a codon selected from the group consisting of AGC, AGU, UCA, UCC, UCG, and UCU.

Another aspect of the present invention includes a method for introducing a loxP site into the chromosome of a cell by introducing a first polynucleotide flanked by loxP sites into the cell under conditions that allow integration of the polynucleotide into the chromosome, introducing a second polynucleotide, encoding a CRE recombinase, in which the second polynucleotide has been modified from the native polynucleotide sequence (SEQ ID NO: 1) to replace at least one of coding sequence leucine residues encoded by a CUG codon with a codon selected from the group consisting of UUA, UUG, CUU, CUC, and CUA under conditions that allow expression of the polypeptide, wherein the polypeptide causes removal of the portion of first polynucleotide between the two loxP sites to form a single loxP site in the chromosome.

In another aspect, the present invention provides a kit for obtaining Cre recombinase expression in a cell comprising a construct containing a selectable marker and the modified polynucleotide encoding a Cre recombinase, in which at least one of the leucine residues encoded by a CUG codon is encoded by a codon selected from the group consisting of UUA, UUG, CUU, CUC, and CUA.

DETAILED DESCRIPTION OF THE INVENTION

The present invention provides methods for expressing non-native polypeptides in *P. stipitis,* as well as methods for expressing polypeptides native to *P. stipitis* in other species. The present invention is based in part on our discovery that *P. stipitis* comprises a tRNA that translates CUG codons as serine rather than leucine.

Until recently, it was axiomatic that all organisms employ the universal genetic code. However, several species of *Candida,* including *Candida shehatae, Candida albicans, Candida guilliermondii, Candida rugosa, Candida tropicalis* and *Candida maltosa,* have been found to use an alternative codon system that translates the CUG codon as serine rather than leucine, as would be expected based on the universal genetic code (Sugita and Nakese, 1999). The use of an alternative nuclear genetic code complicates efforts to carry out heterologous expression of genes in yeasts using this codon system.

As described below in the Examples, appropriate expression of polypeptides containing leucine may be obtained in *P. stipitis* by replacing coding sequences that specify CUG in mRNA with sequences that encode other leucine codons (i.e., UUA, UUG, CUU, CUC, or CUA). Polynucleotides encoding proteins that confer antibiotic resistance or perform other useful functions were genetically engineered using PCR mutagenesis to obtain sequences in which sequences encoding CUG codons were replaced with UUG, which is the most commonly used leucine codon in *P. stipitis*. It is specifically envisioned that one or more of the CUG codons could be replaced with UUA, UUG, CUU, CUC, or CUA, or combinations thereof. A sequence in which fewer than all of the CUG codons are replaced with an alternative leucine codon would be useful as an intermediate in the subsequent development of other coding sequences. It is also envisioned that it may be possible to replace less than all of the CUG codons to obtain a sequence encoding a functional protein.

Coding sequences specifying CUG codons may be replaced with other leucine coding sequences using PCR mutagenesis, as described in the Examples. However, any suitable means of obtaining polynucleotides in which sequences n specifying CUG codons have been replaced may be used, including, for example, the design and synthesis of synthetic oligonucleotides.

Coding sequences suitable for use in the method of the invention may also be obtained by selecting sequences that natively lack sequences that specify CUG codons. Such sequences could be used in the method of the invention without modifying the coding sequence. For example, the native blasticidin resistance coding sequence Blasticidin-S deaminase (Itaya et al. 1990; Kobayashi et al. 1991) blasticidin$^R$ or bsr (SEQ ID NO: 5) does not use the CUG codon to code for leucine, and could be used to impart Blasticidin-S resistance to yeast cells that are normally sensitive to the antibiotic.

Other types of sequences that may be used in the practice of the invention include selected coding sequences that contain a sequence specifying a CUG codon that encodes a serine residue in the native protein. Sequences obtained from organisms in which CUG codons are recognized by serine tRNA are particularly suitable.

As described below, PCR mutagenesis was used to modify the native Sh ble coding sequence from *S. verticuilus* (SEQ ID NO: 7), the expression of which produces a polypeptide (SEQ ID NO: 8) that confers resistance to Phleomycin, bleomycin, and Zeocin, such that the in-frame CTG trinucleotide sequences of the DNA sequences specifying CUG codons were replaced with sequences specifying UUG codons. The modified Sh ble polynucleotide coding sequence is shown in SEQ ID NO: 9 and its translated polypeptide is shown in SEQ ID NO: 10. It is envisioned that the adapted Sh ble gene could be used in any fungus, sensitive to Zeocin, that uses the fungal alternative genetic code and that its expression could be driven by any suitable promoter, including, for example, constitutive or inducible promoters. Replacing the CTG trinucleotides with sequences that encode one of the other leucine coding sequences will permit expression of Sh ble in cells that use the alternative codon system. In addition to modifying the CUG codons, codons specifying other amino acids were modified based on preferred codon usage of *P. stipitis*, the intended host.

Other antibiotic resistance markers may be modified such that sequences specifying CUG codons are replaced with sequences specifying other leucine codons and used to confer antibiotic resistance to organisms employing the alternative coding system (e.g., *P. stipitis*). For example, the native sequences encoding Hygromycin B phosphotransferase (hph) confering resistance to hygromycin and its homologues when expressed in susceptible cells, and neomycin phosphotransferase, a polypeptide that confers neomycin resistance, each comprise CTG trinucleotide sequences of the DNA encoding the leucine codon CUG. The native polynucleotide coding sequences for Hygromycin B phosphotransferase and neomycin phosphotransferase are shown in SEQ ID NO: 11 and SEQ ID NO: 13, respectively. The polypeptide sequences for Hygromycin B phosphotransferase and neomycin phosphotransferase are shown in SEQ ID NO: 12 and SEQ ID NO: 14, respectively. It is envisioned that one or more of the CTG codons would be replaced.

In addition to antibiotic resistance markers, other useful polypeptides not natively associated with *P. stipitis* may be expressed using coding sequences that have been modified such that sequences specifying CUG codons are replaced with sequences specifying other leucine codons. As described in the Examples, site-directed mutagenesis was used to change a the native polynucleotide (SEQ ID NO: 1) encoding the Cre recombinase (SEQ ID NO: 2) by altering sequences specifying CUG codons to sequences specifying UUG codons. Cre recombinase is a bacteriophage P1 protein that mediates site-specific recombination between two 34 base pair loxP sites, and can be used to excise polynucleotides between two loxP sites, or to insert polynucleotides into a loxP site. The Cre coding sequences in which sequences specifying CUG codons are replaced with sequences specifying other leucine codons will allow expression of Cre in organisms that use the alternative codon system, and can therefore be used to either introduce or delete polynucleotides from the chromosome of the cell via the Cre-loxP system.

The present invention permits the introduction of loxP Cre-binding and recombination sites into the chromosome of yeast employing the alternative codon system by homologous recombination using a construct containing loxP Cre-binding and recombination sites and flanked by a sequence with homology to the host cell chromosome. In the Examples below, a XYL2 disruption mutant was made using a construct comprising URA3 flanked by the loxP Cre-binding and recombination sites and by sequences having homology to XYL2. Expression of a modified Cre-recombinase and a Sh ble resistance marker under the control of the constituitive promoter TEF1 resulted in the removal of the URA3 sequence to form a loxP site. The loxP site permits site-specific integration of sequences flanked by loxP Cre-binding and recombination sites in the presence of Cre recombinase. The LoxP-Cre Recombinase system can be used as part of an expression cassette that is transformed into the genome. The URA3 then can be selectively excised, leaving the exogenous sequence in the genome, and allowing further genetic manipulation using the URA3 marker. In addition, a LoxP site already in the genome could be used to place other genes in the same site. It is envisioned that the LoxP-Cre recombinase system can also be used in other yeasts using the fungal alternative genetic code, and with other potential marker genes, such as the adapted Ble gene, an auxotrophic marker or other fungicidal resistant marker. In addition to the use of URA3 as a selective marker in the expression cassette, any selective marker, but most preferably a marker that can be negatively selected, can be used.

It is envisioned that the antibiotic resistance markers may be introduced into a yeast cell and integrated into the chromosome by homologous recombination. In other words, the sequence encoding the antibiotic resistance marker would be delivered into the cell as part of a construct comprising sequences capable of undergoing homologous recombination with a portion of the chromosome of the recipient cell.

A coding sequence selected or modified for use in the present invention is operably connected to a promoter functional in the yeast cell into which the coding sequence will be expressed, such that the promoter allows expression of the coding sequence in the recipient host cell. Any suitable promoter may be used, including, for example, constitutive or inducible promoters. Polypeptide expression may be assessed by a variety of techniques well known in the art including, but not limited to, Western Blot analysis, ELISA, or a functional assay for protein activity (e.g. antibiotic resistance.)

A polynucleotide operably linked to a promoter functional in a yeast cell may be introduced into the yeast cell using any suitable means, including, but not limited to, electroporation, the Bicine method, protoplast formation or Li-Acetate, as described in Example 2. The methods of the invention are useful in transforming yeast cells having alternative codon usage. It is envisioned that the transformation and site-specific integration methods will allow repeated manipulation of cells. In other words, a single selectable marker may be used more than once to permit repeated selection of cells.

It is envisioned that novel polynucleotides described herein may be used with any other organism that employs an alternative codon system, including, but not limited to, Candida shehatae, Candida albicans, Candida guilliermondii, Candida rugosa, Candida tropicalis, Candida maltosa, and Debaromyces hansenii. It is also envisioned that expression of functional P. stipitis polypeptides of interest may be obtained in an organism that employs the conventional codons by expressing in the organism a sequence encoding the polypeptide in which sequences encoding the serine codon CUG is replaced with a conventional serine codon coding sequence.

As described in the Examples, xylose inducible expression of Cre recombinase was obtained in P. stipitis by transforming cells with a construct in which a sequence encoding Cre recombinase was operably linked to a P. stipitis XYL1 promoter. The Xyl1 promoter is an inducible promoter that drives expression of an operably connected polynucleotide in the presence of xylose, but not in the absence of xylose.

In addition, a P. stipitis TEF-1 promoter comprising SEQ ID NO. 15 was identified as a constitutive promoter. As described in Example 3, the TEF-1 promoter was identified in a highly expressed sequence tag analysis using a library made with the Universal Genome Walker™ kit (Promega Corp., Madison, Wis.). The TEF-1 promoter is a novel promoter for carbon metabolism independent expression of heterologous polynucleotides in P. stipitis. The expression of polypeptides according to the present invention may be obtained by using constructs in which the polynucleotide coding sequence is operably linked to a TEF-1 promoter, as described for the sequence encoding ble in the Examples. To identify smaller subfragments of SEQ ID NO: 15 retaining carbon metabolism independent promoter activity, constructs comprising subfragments of SEQ ID NO: 15 operably linked to a reporter polynucleotide (e.g., Green Fluorescence Protein, luciferase, peroxidase, or an antibiotic resistance marker) may be introduced into a cell and the cell screened for the presence or absence of reporter activity.

The following nonlimiting Examples are intended to be purely illustrative.

EXAMPLE 1

Adaptation of Drug Resistance Markers for Use in Yeasts Using CUG (CTG) to Code for Serine Rather than Leucine Overlap extension PCR (Dieffenback and Dveksler, 1995, PCR Primer A Laboratory Manual, p. 603) was used to modify the ORF of the bleomycin resistance marker from S. verticillus such that the in-frame CTG trinucleotides, which encode CUG codons, were replaced with TTG, which encode UUG codons. The 5' or 3' region of the Sh ble ORF was amplified from the pZERO-1 plasmid (Invitrogen) using primers oJML137 (SEQ ID NO: 22) and oJML176B (SEQ ID NO: 26), and oJML177A (SEQ ID NO: 27) and oJML178A (SEQ ID NO: 28), respectively (Table 1). The PCR products were separated by agarose gel electrophoresis, excised, and purified using Quiagen MiniElute Kit as recommended. The PCR products were combined and amplified using TaqGold (ABI Biosystems) using oJML137 (SEQ ID NO: 22) and oJML178A (SEQ ID NO: 28). The sequence was verified by dideoxy method sequencing (UW Biotech Center). The resulting sequence will produce an mRNA transcript which would be correctly translated in organisms that recognize CUG as serine. In addition, codons 51, 59, 69, 209, 113, 116 were modified to encode the more frequently used codons UCC, CCA, AGA, AGA, and GUG, respectively. The resulting polynucleotide is shown in SEQ ID NO. 9.

TABLE 1

| SEQ ID NO. | Primer Name | Sequence 5' → 3' |
|---|---|---|
| 16 | oJML77 | GTGGACTTACCAGAATCGACGTGACCG |
| 17 | oJML78 | GAACCCTTACCCAATTCAGCGGCTTCC |
| 18 | oJML105 | GCGTCTAGAGATCCACAGACACTAATTGGTTC |
| 19 | oJML106 | CGGGATCCTGTAGTATAGTTGTATAGAAAAGAATAC |
| 20 | oJML109 | AACTGCAGGAAGGTTGCTTTATAGAGAGG |
| 21 | oJML110 | GGGAATTCGATATGATGCAGAAGTAGTTTTG |
| 22 | oJML137 | AGATCTATGGCCAAGTTGACCAGTGCC |
| 23 | oJML154 | TCGAGGGGGGGCCCGGTACCATGGAGATCTATGCATCGTAC |
| 24 | oJML155 | CGATGCATAGATCTCCATGGTACCGGGCCCCCCC |
| 25 | oJML158 | GGCTCGAGATCTTCTGCGGTGTCTACAAGG |
| 26 | oJML176B | GGCCAAGGTGTTGTCTGGGACAACCTGGTCCTGGACAGCGGAGATGAACAAGGTCACGTCGTCCCGGACC |
| 27 | oJML177A | CCCAGACAACACCTTGGCCTGGGTGTGGGTGAGAGGCTTGGACGAGTTGTACGCCGAGTGGTCGGAG |
| 28 | oJML178A | GGCTGCAGTCAGTCCTGCTCCTCGGCCACGAAGTGCACGCAGTTACCGGCTGGGTCTCTCAAGGCGAACTCCCGCCCCCAC |
| 29 | oJML235 | GGCTGCAGATTCAGTATAGGATATGGTGTTTAGCAAAATATG |

EXAMPLE 2

Testing for Sensitivity to Zeocin

*Pichia stipitis* UC7 NRRL Y-21448 (2) is a ura3 auxotrophic mutant of *P. stipitis* CBS 6054 (ARS Culture Collection, NRRL USDA Peoria, Ill.). To test if *Pichia stipitis* UC7 is sensitive to Zeocin, UC7 was plated on YPD (Kaiser, Michaelis and Mitchell, 1994) pH 7.5 (1% yeast extract, 2% peptone, 2% dextrose, NaOH to pH 7.5) in the presence of Zeocin (Invitrogen) at a concentration of from 25 µg/ml to 500 µg/ml. Zeocin concentrations of 100 µg/ml or greater killed *Pichia stipitis* UC7.

EXAMPLE 3

Testing of Adapted Sh ble Gene to Confer Resistance to Zeocin

To test if the adapted Sh ble sequence confers resistance to Zeocin, the adapted sequence was placed under the control of the XYL1 promoter and the XYL1 terminator. Three-hundred ninety three (393) bp 3' of the *Pichia stipitis* XYL1 gene was amplified from genomic DNA using primer oJML109 (SEQ ID NO: 20) and oJML110 (SEQ ID NO: 21) and cloned into pCR2.1 (TOPO TA Cloning Kit—Invitrogen), which in turn was subcloned into pJM6 as an EcoR I-EcoR I fragment and the new plasmid was named pJML214. Three hundred fifty eight (358) bp of the 5' untranslated region of the *Pichia stipitis* XYL1 gene was amplified from genomic DNA using primer oJML105 (SEQ ID NO: 18) and oJML106 (SEQ ID NO: 19) and cloned into pCR2.1 (TOPO TA Cloning Kit—Invitrogen), which in turn was digested with Xba I-BamH I. The Xba I-BamH I digest and Blg II-Pst I Sh ble adapted ORF were ligated to pJML214 digested with Xba I and Pst I site of to form pJML343. A similar plasmid was constructed but with the wildtype version for Sh ble to form pJML329. Both plasmids were transformed into a ura3 auxotrophic mutant of CBS6054, UC7 NRRL Y-21448 using a modified Li-Acetate PEG method (Agatep et al. 1998) in which the heat shock was performed at 42° C. for 5 minutes. Transformants were selected in plated on ScD-ura and YPD+Zeocin after four hours of outgrowth in YPD. Only the adapted Sh ble gene conferred resistance to Zeocin. Examples of other strains that could be transformed in a similar manner include but are not limited to *P. stipitis* FPL-UC16 (ura3) NRRL Y-21449. *P. stipitis* FPL-UB1 (ura3) NRRL-Y-21447, *P. stipitis* FPL-PSU1 (ura3) NRRL Y-21446, *Candida shehatae* FPL-CSU12 (ura3) NRRL Y-21450 and *C. shehatae* FPL-CSU18 (ura3) NRRL Y-21451 The plasmid pJML533 can also be used to express genes in a wild-type *Pichia stipitis* that does not contain auxotrophic mutations.

EXAMPLE 4

Identification and Cloning of the TEF1 Promoter

*Pichia stipitis* CBS6054 was grown at 30° C. in either YPD or YPX (1% peptone, 2% yeast extract, 2% xylose) in 200 ml in either 2.8 L flask 300 rpm or a 500 ml flask at 50 rpm. Cells were pelleted by centrifugation at 4° C. and 10,000 rpm. Cells were resuspended in water, centrifuged at 3,000 rpm for 5 min, and frozen in liquid $N_2$. Total RNA was extracted using RNeasy Maxi Kit (Invitrogen) and polyA mRNA was isolated using Oligotex mRNA Maxi Kit (Invitrogen). An EST library was constructed using the Smart cDNA Library Constuction Kit (Clontech). Individual plaques were used to inoculate a culture of XL-1 Blue (2 ml LB+$MgSO_4$ media inoculated 3 hours earlier with 10 µl of an overnight culture of XL-1 Blue, incubated for 15 minutes at 37° C. with shaking, no shaking for 30 minutes and overnight with shaking. One µl of the supernatant was used as template for PCR.

The insert of each clone was amplified using PCR and 5' pTRip1EX2 and 3' pTRip1EX2 (Clontech) as primers. The amplification products were treated with Exo-Sap1 (USB) to digest and dephosphorylate unused primers. The PCR products were sequences using the dideoxy method and 5' pTrip1EX2 as primer. 965 individuals phage were sequenced, and 678 gave readable sequence. Of those, 16 encoded a protein with high identity to *Saccharomyces cerevisiae* Tef1p.

A genome walker library was constructed as described in Ultimate Genome Walker Kit (BD Biosciences Clontech) and additional libraries constructed using Hpa I, Msc I, PmL I, Sma I, Ssp I and Stu I (New England Biolabs) as restriction enzymes. More than 700 bp downstream of the TEF1 promoter was amplified as described in the Ultimate Genome Walker Kit using primers oJML77 (SEQ ID NO: 16) and oJML78 (SEQ ID NO: 17) and AmpliTaq Gold (Applied Biosystems). Sequencing was performed using the dideoxy method at the University of Wisconsin Biotech Center.

EXAMPLE 5

Construction of Plasmids for the Expression of Genes in *Pichia stipitis* pBluescript KS II- (Strategene) was modified by adding Nco I, Bgl II, and Nsi I sites flanking Kpn I of the multiple cloning site. Oligos oJML154 (SEQ ID NO: 23) and oJML155 (SEQ ID NO: 24 ) were combined and phosphorylated with T4 Polynucleotide Kinase (NEB Biolabs) and ligated into the Xho I-Kpn I sites of pBluescript KS II-. The multiple cloning site sequence was verified by sequencing using the dideoxy method at the University of Wisconsin Biotech Center. PsURA3 was modified to eliminate Sal I, Hind III, Eco RI, and Kpn I restriction enzyme sites using a similar method to create a PsURA3 sequence (PsURA3m) that lacks these restriction sites (SEQ ID NO: 30). The final segment was flanked by Nsi I-Sal I sites. PsARS2 flanked by Pst I-Xho I was amplified from genomic DNA using primer oJML158 (SEQ ID NO: 25) and oJML235 (SEQ ID NO: 29). The adapted Ble-gene was placed in translational fusion with the TEF1 promoter (700 bp) and 458 bp of the 3' untranslated region of *P. stipitis* XYL2 gene. This fragment was flanked with Sal I-Kpn I restriction sites. pJML447 was made by ligating the URA3 Nsi I-Sal I fragment with the Pst I-Xho I ARS2 fragment into the Nsi I-Kpn I site of pJML295. pJML533 was constructed in a similar method using the pTEF1-BLE-tXYL2 Nsi I-Sal I fragment instead of the URA3 fragment. These plasmids have the multiple cloning site of pBluescript KS II- but now can be used as cloning vectors in *P. stipitis*.

EXAMPLE 6

Adaptation of Codon Usage in the Gene for CRE Recombinase

The CUG codons in the Cre-recombinase were adapted in a similar manner as the Sh ble gene described in Example 1. In addition to the 18 CTG trinucleotides that were change to TTG, codons 16, 24, 32, 34, 36, 45, 95, 100, 101, 106, 119, 164, 216, 223, 234, 263, 270, 333, 337, and 342 were changed to the more frequently used codons CCA, AGA, AGA, AGA, GCT, TTA, TTG, AGA, CGT, AGA, AGA, GGT, GGT, AGA, CCA, GGT, AGA, GGT, AGA, and GGT, respectively. The modified Cre-recombinase coding sequence is shown in SEQ ID NO: 3.

EXAMPLE 7

Deletion of a Target Gene (XYL2) Using a Selectable Marker Flanked by loxP Sequences A disruption cassette was constructed containing bases 350 to 161 of the 5' region of the *P. stipitis* XYL2 gene and bases 935 to 1490 of the 3' region of the XYL2 gene with the PsURA3 flanked by the loxP sites. In our experience, at least 400 bp of flanking region is required to achieve efficient homologous recombination. This disruption cassette was transformed into *P. stipitis* UC7 using a modified Li-Acetate transformation protocol (see Example 3), and ura+ colonies were selected on ScD-ura plates. A secondary screen was performed on xylose plates. Putative site-specific disruptants were identified by their slow growth on xylose. A Δxyl2::LoxP-URA3-LoxP was identified by amplification of the XYL2 loci using primers that anneal to the outside of the disruption cassette.

EXAMPLE 8

Excision of the Selectable Marker Using the Adapted CRE

The mutated Cre-Recombinase was placed under the control of 393 bp XYL1 promoter in a plasmid containing the adapted Sh ble gene under the control of the TEF1 promoter (pJML535). The XYL1 promoter was chosen to drive transcription because it is inducible. The plasmid was transformed using the Bicine method (Wolf, Breunig and Barth, 2003) and transformants selected in YPD (pH 7.5) with 100
r μg/ml of Zeocin. Transformants were then grown in YPX overnight and ura- colonies selected by plating in ScD+FOA plates. Removal of the URA3 gene from the XYL2 loci was verified by PCR amplification. The URA3 markermay be used to disrupt other genes

LIST OF PUBLICATIONS CITED

Agatep, R., R. D. Kirkpatrick, D. L parchaliuk, R. A. Woods, and R. D. Gietz 1998, posting Date. Transformation of Saccharomyces cerevisiae by the lithium acetate/single-strand Carrier DNA/polyethylene glycol (LiAc/ss-DNA/PEG) protocol.Technical Tips Online.
[Online.]
Yang, V. W., J. A. Marks, B. P. Davis, and T. W. Jeffries. 1994. High-efficiency Transformation of *Pichia stipitis* based on its URA3 gene and a homologous autonomous Replication sequence, ARS2. Appl Environ Microbiol 60:4245-54.
Lu, P., Davis, B.P., Hendrick, J.Jeffries,T.W.1998. Cloning and disruption of the beta-isopropylmalate dehydrogenase gene (LEU2) of *Pichia stipitis* with URA3 and recovery of the double auxotroph. *Appl. Microbiol. Biotechnol.* 49:141-146.
Methods in Yeast Genetics A Cold Spring Harbor Laboratory Course Manual, Edited by Chris Kaiser, Susan Michaelis, and Aaaron Mitchell. Cold Spring Harbor Press 1994
PCR Primer A Laboratory Manual Edited by Carl W. Dieffenbach and Gabriela S. Dveksler. Cold Spring Harbor Laboratory Press 1995
Non-Conventional Yeast in Genetics, Biochemistry and Biotechnology, Edited by Klaus Wolf, Karin Breuning, and Gerold Barth. Springer2003
Agatep, R., R. D. Kirpatrick, D.L. Parchaliuk, R.A. Wood, and R.D. Gietz (1998) Transformation of *Saccharomyces cerevisiae* by the lithium acetate/single-stranded carrier DNA/polyethylene glycol (LiAc/ss-DNA/PEG) protocol. Technical Tips Online (http://tto. trends.com)

We claim:

1. A yeast comprising a polynucleotide encoding a Cre recombinase of SEQ ID NO: 2, wherein at least one leucine residue at amino acid numbers 27, 46, 83, 104, 115, 161, 164, 171, 203, 215, 220, 238, 261, 284, 328, 338, and 339 is encoded by a codon selected from the group consisting of UUA, UUG, CUU, CUC, and CUA, and wherein the yeast is *Pichia stipitis*.

2. The yeast of claim 1, comprising the polynucleotide encoding a Cre recombinase of SEQ ID NO:2, wherein at least one of the leucine residues at amino acid numbers 27, 46, 83, 104, 115, 161, 164, 171, 203, 215, 220, 238, 261, 284, 328, 338, and 339 is encoded by UUG.

3. The yeast of claim 1, comprising the polynucleotide encoding a Cre recombinase of SEQ ID NO:2, wherein the leucine residues at amino acid numbers 27, 46, 83, 104, 115, 161, 164, 171, 203, 215, 220, 238, 261, 284, 328, 338, and 339 is encoded by UUA, UUG, CUU, CUC, and CUA.

4. The yeast of claim 1, comprising the polynucleotide encoding a Cre recombinase of SEQ ID NO:2, wherein the leucine residues at amino acid numbers 27, 46, 83, 104, 115, 161, 164, 171, 203, 215, 220, 238, 261, 284, 328, 338, and 339 are encoded by UUG.

5. A kit for obtaining expression of Cre recombinase in a *Pichia stipitis*, comprising the yeast of claim 1.

* * * * *

UNITED STATES PATENT AND TRADEMARK OFFICE
CERTIFICATE OF CORRECTION

PATENT NO. : 7,501,275 B2
APPLICATION NO. : 10/973274
DATED : March 10, 2009
INVENTOR(S) : Jose M. Laplaza and Thomas W. Jeffries It is certified that error appears in the above-identified patent and that said Letters Patent is hereby corrected as shown below:

In the Specification

Column 8: line 48, change "pJML447" to --pJML457--.
Column 9: line 34, change "pJML535" to --pJML533--.

Signed and Sealed this
Fifteenth Day of October, 2013

Teresa Stanek Rea
*Deputy Director of the United States Patent and Trademark Office*

SEQUENCE LISTING

<160> NUMBER OF SEQ ID NOS: 30

<210> SEQ ID NO 1
<211> LENGTH: 1032
<212> TYPE: DNA
<213> ORGANISM: Enterobacteria phage P1

<400> SEQUENCE: 1

```
atgtccaatt tactgaccgt acaccaaaat ttgcctgcat taccggtcga tgcaacgagt      60
gatgaggttc gcaagaacct gatggacatg ttcagggatc gccaggcgtt ttctgagcat     120
acctggaaaa tgcttctgtc cgtttgccgg tcgtgggcgg catggtgcaa gttgaataac     180
cggaaatggt ttcccgcaga acctgaagat gttcgcgatt atcttctata tcttcaggcg     240
cgcggtctgg cagtaaaaac tatccagcaa catttgggcc agctaaacat gcttcatcgt     300
cggtccgggc tgccacgacc aagtgacagc aatgctgttt cactggttat gcggcggatc     360
cgaaaagaaa acgttgatgc cggtgaacgt gcaaaacagg ctctagcgtt cgaacgcact     420
gatttcgacc aggttcgttc actcatggaa aatagcgatc gctgccagga tatacgtaat     480
ctggcatttc tggggattgc ttataacacc ctgttacgta tagccgaaat tgccaggatc     540
agggttaaag atatctcacg tactgacggt gggagaatgt taatccatat tggcagaacg     600
```

```
aaaacgctgg ttagcaccgc aggtgtagag aaggcactta gcctgggggt aactaaactg    660
gtcgagcgat ggatttccgt ctctggtgta gctgatgatc cgaataacta cctgttttgc    720
cgggtcagaa aaaatggtgt tgccgcgcca tctgccacca gccagctatc aactcgcgcc    780
ctggaaggga ttttttgaagc aactcatcga ttgatttacg gcgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatt ag                                                        1032
```

<210> SEQ ID NO 2
<211> LENGTH: 343
<212> TYPE: PRT
<213> ORGANISM: Enterobacteria phage P1

<400> SEQUENCE: 2

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
```

```
              290                 295                 300
Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 3
<211> LENGTH: 1032
<212> TYPE: DNA
<213> ORGANISM: Enterobacteria phage P1

<400> SEQUENCE: 3
atgtccaatt tattgaccgt acaccaaaat ttgcctgcat taccagtcga tgcaacgagt      60
gatgaggtta gaaagaactt gatggacatg ttcagagata cacaggcttt ttctgagcat     120
acctggaaaa tgttattgtc cgtttgccgg tcgtgggcgg catggtgcaa gttgaataac     180
cggaaatggt ttcccgcaga acctgaagat gttcgcgatt atcttctata tcttcaggcg     240
cgcggtttgg cagtaaaaac tatccagcaa catttgggcc agttgaacat gcttcataga     300
cgttccgggt tgccaagacc aagtgacagc aatgctgttt cattggttat gcggagaatc     360
cgaaaagaaa acgttgatgc cggtgaacgt gcaaaacagg ctctagcgtt cgaacgcact     420
gatttcgacc aggttcgttc actcatggaa aatagcgatc gctgccagga tatacgtaat     480
ttggcatttt tgggtattgc ttataacacc ttgttacgta tagccgaaat tgccaggatc     540
agggttaaag atatctcacg tactgacggt gggagaatgt taatccatat tggcagaacg     600
aaaacgttgg ttagcaccgc aggtgtagag aaggcactta gcttgggtgt aactaaattg     660
gtcgagagat ggatttccgt ctctggtgta gctgatgatc caaataacta cttgttttgc     720
cgggtcagaa aaaatggtgt tgccgcgcca tctgccacca gccagctatc aactcgcgcc     780
ttggaaggta ttttgaagc aactcataga ttgatttacg gcgctaagga tgactctggt     840
cagagatact tggcctggtc tggacacagt gcccgtgtcg gagccgcgcg agatatggcc     900
cgcgctggag tttcaatacc ggagatcatg caagctggtg gctggaccaa tgtaaatatt     960
gtcatgaact atatccgtaa cttggatagt gaaacaggtg caatggtgag attgttggaa    1020
gatggtgatt ag                                                        1032

<210> SEQ ID NO 4
<211> LENGTH: 343
<212> TYPE: PRT
<213> ORGANISM: Enterobacteria phage P1

<400> SEQUENCE: 4

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
```

-continued

```
                85                  90                  95
Met Leu His Arg Arg Ser Gly Leu Pro Arg Pro Ser Asp Ser Asn Ala
            100                 105                 110
Val Ser Leu Val Met Arg Arg Ile Arg Lys Glu Asn Val Asp Ala Gly
            115                 120                 125
Glu Arg Ala Lys Gln Ala Leu Ala Phe Glu Arg Thr Asp Phe Asp Gln
        130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
        210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
        290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
            340
```

```
<210> SEQ ID NO 5
<211> LENGTH: 423
<212> TYPE: DNA
<213> ORGANISM: Escherichia coli

<400> SEQUENCE: 5
atgaaaacat ttaacatttc tcaacaagat ctagaattag tagaagtagc gacagagaag      60
attacaatgc tttatgagga taataaacat catgtgggag cggcaattcg tacgaaaaca     120
ggagaaatca tttcggcagt acatattgaa gcgtatatag gacgagtaac tgtttgtgca     180
gaagccattg cgattggtag tgcagtttcg aatggacaaa aggattttga cacgattgta     240
gctgttagac acccttattc tgacgaagta gatagaagta ttcgagtggt aagtccttgt     300
ggtatgtgta gggagttgat ttcagactat gcaccagatt gttttgtgtt aatagaaatg     360
aatggcaagt tagtcaaaac tacgattgaa gaactcattc cactcaaata tacccgaaat     420
taa                                                                   423
```

```
<210> SEQ ID NO 6
<211> LENGTH: 140
<212> TYPE: PRT
<213> ORGANISM: Escherichia coli
```

<400> SEQUENCE: 6

Met Lys Thr Phe Asn Ile Ser Gln Gln Asp Leu Glu Leu Val Glu Val
1               5                   10                  15

Ala Thr Glu Lys Ile Thr Met Leu Tyr Glu Asp Asn Lys His His Val
                20                  25                  30

Gly Ala Ala Ile Arg Thr Lys Thr Gly Glu Ile Ile Ser Ala Val His
            35                  40                  45

Ile Glu Ala Tyr Ile Gly Arg Val Thr Val Cys Ala Glu Ala Ile Ala
50                  55                  60

Ile Gly Ser Ala Val Ser Asn Gly Gln Lys Asp Phe Asp Thr Ile Val
65                  70                  75                  80

Ala Val Arg His Pro Tyr Ser Asp Glu Val Asp Arg Ser Ile Arg Val
                85                  90                  95

Val Ser Pro Cys Gly Met Cys Arg Glu Leu Ile Ser Asp Tyr Ala Pro
            100                 105                 110

Asp Cys Phe Val Leu Ile Glu Met Asn Gly Lys Leu Val Lys Thr Thr
        115                 120                 125

Ile Glu Glu Leu Ile Pro Leu Lys Tyr Thr Arg Asn
    130                 135                 140

<210> SEQ ID NO 7
<211> LENGTH: 369
<212> TYPE: DNA
<213> ORGANISM: Streptomyces verticillus

<400> SEQUENCE: 7
atggtgaaat tcacgggtgc catcccggtc ctgaccgccg tcgacgtacc ggccggcgtc      60
gccttctggg tcggcacgct gggtttcgag gaggacttcg ccgacgacgg cttcgcgggc     120
atccaccgcg gcgacgtaca gctcttcatc agccggacgg aacaccagct cgtcgcggac     180
aacacctccg cgtgggtgga ggtcctgggc ctcgacgaac tgcacgcgca gtggtcacag     240
gtgctctcca ccgactacgc ggacgcctcg ggcccggcca tgaccgcggt gacggacacc     300
ccttggggcc gtgagttcgc ggtgcgcgac ccggccggga actgcgtcca cttcgccgcc     360
gagcactga                                                             369

<210> SEQ ID NO 8
<211> LENGTH: 122
<212> TYPE: PRT
<213> ORGANISM: Streptomyces verticillus

<400> SEQUENCE: 8

Met Val Lys Phe Thr Gly Ala Ile Pro Val Leu Thr Ala Val Asp Val
1               5                   10                  15

Pro Ala Gly Val Ala Phe Trp Val Gly Thr Leu Gly Phe Glu Glu Asp
                20                  25                  30

Phe Ala Asp Asp Gly Phe Ala Gly Ile His Arg Gly Asp Val Gln Leu
            35                  40                  45

Phe Ile Ser Arg Thr Glu His Gln Leu Val Ala Asp Asn Thr Ser Ala
50                  55                  60

Trp Val Glu Val Leu Gly Leu Asp Glu Leu His Ala Gln Trp Ser Gln
65                  70                  75                  80

Val Leu Ser Thr Asp Tyr Ala Asp Ala Ser Gly Pro Ala Met Thr Ala
                85                  90                  95

Val Thr Asp Thr Pro Trp Gly Arg Glu Phe Ala Val Arg Asp Pro Ala

Gly Asn Cys Val His Phe Ala Ala Glu His
        115                 120

<210> SEQ ID NO 9
<211> LENGTH: 375
<212> TYPE: DNA
<213> ORGANISM: Streptomyces verticillus

<400> SEQUENCE: 9

| | | | | | |
|---|---|---|---|---|---|
| atggccaagt | tgaccagtgc | cgttccggtg | ctcaccgcgc | gcgacgtcgc | cggagcggtc | 60 |
| gagttctgga | ccgaccggct | cgggttctcc | cgggacttcg | tggaggacga | cttcgccggt | 120 |
| gtggtccggg | acgacgtgac | cttgttcatc | tccgctgtcc | aggaccaggt | tgtcccagac | 180 |
| aacaccttgg | cctgggtgtg | ggtgagaggc | ttggacgagt | tgtacgccga | gtggtcggag | 240 |
| gtcgtgtcca | cgaacttccg | ggacgcctcc | gggccggcca | tgaccgagat | cggcgagcag | 300 |
| ccgtgggggc | gggagttcgc | cttgagagac | ccagccggta | actgcgtgca | cttcgtggcc | 360 |
| gaggagcagg | actga | | | | | 375 |

<210> SEQ ID NO 10
<211> LENGTH: 124
<212> TYPE: PRT
<213> ORGANISM: Streptomyces verticillus

<400> SEQUENCE: 10

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 11
<211> LENGTH: 1026
<212> TYPE: DNA
<213> ORGANISM: Escherichia coli

<400> SEQUENCE: 11

| | | | | | |
|---|---|---|---|---|---|
| atgaaaaagc | tgaactcac | cgcgacgtct | gtcgagaagt | ttctgatcga | aaagttcgac | 60 |
| agcgtctccg | acctgatgca | gctctcggag | ggcgaagaat | ctcgtgcttt | cagcttcgat | 120 |
| gtaggagggc | gtggatatgt | cctgcgggta | aatagctgcg | ccgatggttt | ctacaaagat | 180 |
| cgttatgttt | atcggcactt | tgcatcggcc | gcgctcccga | ttccgaagt | gcttgacatt | 240 |
| ggggaattca | gcgagagcct | gacctattgc | atctcccgcc | gtgcacaggg | tgtcacgttg | 300 |
| caagacctgc | ctgaaaccga | actgcccgct | gttctgcagc | cggtcgcgga | ggccatggat | 360 |

```
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 12
<211> LENGTH: 341
<212> TYPE: PRT
<213> ORGANISM: Escherichia coli

<400> SEQUENCE: 12

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255
```

-continued

```
Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 13
<211> LENGTH: 816
<212> TYPE: DNA
<213> ORGANISM: Escherichia coli

<400> SEQUENCE: 13
atgagccata ttcaacggga aacgtcttgc tccaggccgc gattaaattc aacatggat       60 gctgatttat atgggtataa atgggcacgc gataatgtcg ggcaatcagg tgcgacaatc      120
tatcgattgt atgggaagcc cgatgcgcca gagttgtttc tgaaacatgg caaaggtagc      180
gttgccaatg atgttacaga tgagatggtc agactaaact ggctgacgga atttatgcct      240
cttccgacca tcaagcattt tatccgtact cctgatgatg catggttact caccactgcg      300
atccccggca aaacagcatt ccaggtatta agaatatc ctgattcagg tgaaaatatt       360
gttgatgcgc tggcagtgtt cctgcgccgg ttgcattcga ttcctgtttg taattgtcct      420
tttaacagcg atcgcgtatt tcgtctcgct caggcgcaat cacgaatgaa taacggtttg      480
gttgatgcga gtgattttga tgacgagcgt aatggctggc ctgttgaaca gtctggaaa      540 gaaatgcata agctcttgcc attctcaccg gattcagtcg tcactcatgg tgatttctca      600
cttgataacc ttatttttga cgaggggaaa ttaataggtt gtattgatgt ggacgagtc       660 ggaatcgcag accgatacca ggatcttgcc atcctatgga actgcctcgg tgagttttct      720
ccttcattac agaaacggct ttttcaaaaa tatggtattg ataatcctga tatgaataaa      780
ttgcagtttc atttgatgct cgatgagttt ttctaa                                816

<210> SEQ ID NO 14
<211> LENGTH: 271
<212> TYPE: PRT
<213> ORGANISM: Escherichia coli

<400> SEQUENCE: 14

Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
```

```
                    85                  90                  95
Leu Thr Thr Ala Ile Pro Gly Lys Thr Ala Phe Gln Val Leu Glu Glu
                100                 105                 110
Tyr Pro Asp Ser Gly Glu Asn Ile Val Asp Ala Leu Ala Val Phe Leu
            115                 120                 125
Arg Arg Leu His Ser Ile Pro Val Cys Asn Cys Pro Phe Asn Ser Asp
        130                 135                 140
Arg Val Phe Arg Leu Ala Gln Ala Gln Ser Arg Met Asn Asn Gly Leu
145                 150                 155                 160
Val Asp Ala Ser Asp Phe Asp Asp Glu Arg Asn Gly Trp Pro Val Glu
                165                 170                 175
Gln Val Trp Lys Glu Met His Lys Leu Leu Pro Phe Ser Pro Asp Ser
                180                 185                 190
Val Val Thr His Gly Asp Phe Ser Leu Asp Asn Leu Ile Phe Asp Glu
            195                 200                 205
Gly Lys Leu Ile Gly Cys Ile Asp Val Gly Arg Val Gly Ile Ala Asp
        210                 215                 220
Arg Tyr Gln Asp Leu Ala Ile Leu Trp Asn Cys Leu Gly Glu Phe Ser
225                 230                 235                 240
Pro Ser Leu Gln Lys Arg Leu Phe Gln Lys Tyr Gly Ile Asp Asn Pro
                245                 250                 255
Asp Met Asn Lys Leu Gln Phe His Leu Met Leu Asp Glu Phe Phe
                260                 265                 270

<210> SEQ ID NO 15
<211> LENGTH: 700
<212> TYPE: DNA
<213> ORGANISM: Pichia stipitis

<400> SEQUENCE: 15
atacttatgg acaaggttca ctgatttgga ctgaaaagca aaaacgagaa atgagtcaac    60
gtctgagatc aatccctaga ccacccggga aggtcatgtg tttcatgaag tacgataagg   120
ttggtaaccg attgactcat tggttcgtgg cggagaagta cgcagagtaa aaccggggcc   180
gattcgtggt aaattctgga atgatccaga ggcgcgacat ttatgcagac aatttgtgtt   240
ttgtcgcaaa cgatgttata gcgaaatttt tcactctgtc agataaatgg attttgtcaa   300
aaggggggaag tagaaggaga atgggcccga gatgttctgc caaattctca gtagcataat   360
gtgaaagaag cccttacatt gtccagcctc tggcatcatt aaaaaccgta gcggaaacca   420
attgtctctg ttcttccctg gcacaccctg gtagccccat ccagttgtag tacatctcac   480
acgctggcaa cttgggacaa tcagcaactt ttttttcttt taattttttc agcgcgacat   540
tttgcctctt ctgcgagaac agacttttc acctccatct cacccccctt tgcacttata    600
taaattggac cagttcctcc cattgtagaa aaaattttgc tggaccttt tctctttttt    660
ttgtccttta gtttcataca atctaagtct atctacaatg                         700

<210> SEQ ID NO 16
<211> LENGTH: 27
<212> TYPE: DNA
<213> ORGANISM: Pichia stipitis

<400> SEQUENCE: 16
gtggacttac cagaatcgac gtgaccg                                        27

<210> SEQ ID NO 17
```

```
<210> SEQ ID NO 17
<211> LENGTH: 27
<212> TYPE: DNA
<213> ORGANISM: Pichia stipitis

<400> SEQUENCE: 17
gaacccttac ccaattcagc ggcttcc                                              27

<210> SEQ ID NO 18
<211> LENGTH: 32
<212> TYPE: DNA
<213> ORGANISM: Pichia stipitis

<400> SEQUENCE: 18
gcgtctagag atccacagac actaattggt tc                                        32

<210> SEQ ID NO 19
<211> LENGTH: 36
<212> TYPE: DNA
<213> ORGANISM: Pichia stipitis

<400> SEQUENCE: 19
cgggatcctg tagtatagtt gtatagaaaa gaatac                                    36

<210> SEQ ID NO 20
<211> LENGTH: 29
<212> TYPE: DNA
<213> ORGANISM: Pichia stipitis

<400> SEQUENCE: 20
aactgcagga aggttgcttt atagagagg                                            29

<210> SEQ ID NO 21
<211> LENGTH: 31
<212> TYPE: DNA
<213> ORGANISM: Pichia stipitis

<400> SEQUENCE: 21
gggaattcga tatgatgcag aagtagtttt g                                         31

<210> SEQ ID NO 22
<211> LENGTH: 27
<212> TYPE: DNA
<213> ORGANISM: Streptomyces verticillus

<400> SEQUENCE: 22
agatctatgg ccaagttgac cagtgcc                                              27

<210> SEQ ID NO 23
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 23
tcgagggggg gcccggtacc atggagatct atgcatcgta c                              41

<210> SEQ ID NO 24
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 24
```

```
cgatgcatag atctccatgg taccgggccc cccc                                      34

<210> SEQ ID NO 25
<211> LENGTH: 30
<212> TYPE: DNA
<213> ORGANISM: Pichia stipitis

<400> SEQUENCE: 25
ggctcgagat cttctgcggt gtctacaagg                                           30

<210> SEQ ID NO 26
<211> LENGTH: 70
<212> TYPE: DNA
<213> ORGANISM: Streptomyces verticillus

<400> SEQUENCE: 26
ggccaaggtg ttgtctggga caacctggtc ctggacagcg agatgaaca aggtcacgtc           60 gtcccggacc                                                                 70

<210> SEQ ID NO 27
<211> LENGTH: 67
<212> TYPE: DNA
<213> ORGANISM: Streptomyces verticillus

<400> SEQUENCE: 27
cccagacaac accttggcct gggtgtgggt gagaggcttg gacgagttgt acgccgagtg          60
gtcggag                                                                    67

<210> SEQ ID NO 28
<211> LENGTH: 81
<212> TYPE: DNA
<213> ORGANISM: Streptomyces verticillus

<400> SEQUENCE: 28
ggctgcagtc agtcctgctc ctcggccacg aagtgcacgc agttaccggc tgggtctctc          60
aaggcgaact cccgcccccca c                                                   81

<210> SEQ ID NO 29
<211> LENGTH: 42
<212> TYPE: DNA
<213> ORGANISM: Pichia stipitis

<400> SEQUENCE: 29
ggctgcagat tcagtatagg atatggtgtt tagcaaaata tg                             42

<210> SEQ ID NO 30
<211> LENGTH: 1486
<212> TYPE: DNA
<213> ORGANISM: Pichia stipitis

<400> SEQUENCE: 30
acttgaagct cttgatttct acaatgcatc agctacgcgt tcatacaaac cctccataac          60
cttgtactac aactcataca ttgatacata taaccaaatc cttaggatga agacaaaatc         120
aaagttgact tggtatcaaa tggcatacaa aggttttgtc cgcaatgcat tgacaacaat         180
accggctaca tccgtggccc tcttggtttt tgaaataatg agaaccagat tgactgacga         240
cttactggaa ttagaaattt tggaataggc ctctgcttgt aaataatcat atagttgttt         300
gtaaatactt aacgatgtac attacagttt tacgattttt acaaaatttt acatatttta         360
```

```
cacttggctt gtcttcttca agtaagcgtt ccatccagct tctctgtatc tttggccctc    420
tacatcagga tctctaccct tgccgaataa gcctctacca acaatgataa tatcggttcc    480
tgtggaaaca acttcatcta ctgttctata ttgttgacct aaactgtcac ccttgtcatc    540
caaaccgaca ccaggagtca taacaatcca atcgaaacct tcatcttgtc cacccatgtc    600
tctttgggca atgaacccaa taacaaactc tttgtcagtt ttggcgattt ccacagtttc    660
ttcagtatac ttaccatgag caatcgagcc cttagaagat agttcggcaa gcatcaataa    720
acctcttggt tcgtcggtag tttctcttgc agcttccttt aatccctgaa caataccaga    780
accagtaaca cgtgagcatt gggatatctg accattgggc aatcttgtag actccacccg    840
gaatactgag acttgacagg gtttccaagt ctgcgaattt tacgaccttc aaagatcatg    900
aagttgtgct tcttggacaa ttccaacaaa ggaacaatag taccttcata cgaaaaatcg    960
tcgataatgt cgatatgggt cttaaccaaa caaatgtaag gacccaactt atcaatcaaa   1020
gataagaact cagaggttgt tttcacatcc actgaagcac acaagttagt tttcttgctg   1080
tccattaatt tgaagagacg ctgtgctacc ggtgactggt gagactcggc cctttgtgta   1140
taggtttgga cgttgaccat tgtcgaatgt ttttagggtg ttgctagtac acaaagaaag   1200
tctgtgatga attgaaaatt tgtttgtaga tactataaaa tagactaaaa tattttcgc   1260 actgtttgag atgcaacata aacttgctat atttatgaaa gtaactaaaa tacaaaatac   1320
tacttctcca taacgactac tttcttaaga aaccattaga ttacataagt gtaatattta   1380
ttgcagatta gttatctccg tctgtttcga ttttcttctc ttctccaccc tcagcagccg   1440
tgtcgagtat attctcttta ttcttctcag acaacggctc cggatc                  1486
```